(12) United States Patent
Hága et al.

(10) Patent No.: US 11,964,187 B2
(45) Date of Patent: Apr. 23, 2024

(54) DETECTION SYSTEMS AND METHODS

(71) Applicant: Telefonaktiebolaget LM Ericsson (publ), Stockholm (SE)

(72) Inventors: Péter Hága, Budapest (HU); Nóra Fenyvesi, Budapest (HU); Zsófia Kallus, Budapest (HU)

(73) Assignee: TELEFONAKTIEBOLAGET LM ERICSSON (PUBL), Stockholm (SE)

( * ) Notice: Subject to any disclaimer, the term of this patent is extended or adjusted under 35 U.S.C. 154(b) by 1172 days.

(21) Appl. No.: 16/475,202

(22) PCT Filed: Jan. 26, 2017

(86) PCT No.: PCT/EP2017/051661
§ 371 (c)(1),
(2) Date: Jul. 1, 2019

(87) PCT Pub. No.: WO2018/137767
PCT Pub. Date: Aug. 2, 2018

(65) Prior Publication Data
US 2020/0222758 A1    Jul. 16, 2020

(51) Int. Cl.
*A63B 24/00*    (2006.01)
*A63B 71/06*    (2006.01)
(Continued)

(52) U.S. Cl.
CPC ...... *A63B 24/0021* (2013.01); *A63B 24/0006* (2013.01); *G06N 20/00* (2019.01);
(Continued)

(58) Field of Classification Search
CPC ............ A63B 24/0021; A63B 71/0605; G06F 3/0346
See application file for complete search history.

(56) References Cited

U.S. PATENT DOCUMENTS

| 784,669 | A  | 3/1905  | Fiddes et al. |
| 7,854,669 | B2 | 12/2010 | Marty et al. |

(Continued)

FOREIGN PATENT DOCUMENTS

| CN | 101195072 A | 6/2008  |
| CN | 104225891 A | 12/2014 |

(Continued)

*Primary Examiner* — Alvin A Hunter
*Assistant Examiner* — Christopher Glenn
(74) *Attorney, Agent, or Firm* — COATS & BENNETT, PLLC

(57) ABSTRACT

We generally describe a detection system and a method for tracking a moving object. The detection system (101) comprises a sensor (102) which is configured to sense an event. The system further comprises a trigger detection module (108a) which is coupled to the sensor (102), wherein the trigger detection module (108a) is configured to identify the sensed event to be a trigger event. The system further comprises an imaging device (114) for imaging the trajectory of an object, and an imaging device control unit (112) for controlling the imaging device (114). The imaging device control unit (112) is coupled to the trigger detection module (180a), wherein the imaging device control unit (112) is configured to control the imaging device (114) in response to a trigger event being identified by the trigger detection module (108a). The imaging device (114) is coupled to the imaging device control unit (112) for providing a feedback from the imaging device (114) to the imaging device control unit (112), wherein the controlling of the imaging device (114) by the imaging device control unit (112) is responsive to the feedback.

19 Claims, 7 Drawing Sheets

(51) Int. Cl.
*G06N 5/04* (2023.01)
*G06N 20/00* (2019.01)
*G09B 19/00* (2006.01)

(52) U.S. Cl.
CPC .. *G09B 19/0038* (2013.01); *A63B 2024/0012* (2013.01); *A63B 2024/0025* (2013.01); *A63B 2024/0034* (2013.01); *A63B 2024/004* (2013.01); *A63B 2024/0043* (2013.01); *A63B 2024/0056* (2013.01); *A63B 71/06* (2013.01); *A63B 2220/05* (2013.01); *A63B 2220/806* (2013.01); *A63B 2220/807* (2013.01); *A63B 2225/50* (2013.01); *G06N 5/04* (2013.01)

(56) References Cited

U.S. PATENT DOCUMENTS

| | | | | |
|---|---|---|---|---|
| 2001/0023209 A1* | 9/2001 | Yamamoto | ......... | A63B 24/0021 473/190 |
| 2001/0056000 A1* | 12/2001 | Hori | ......... | A63B 47/002 473/453 |
| 2002/0085213 A1* | 7/2002 | Yamamoto | ......... | G01S 3/784 356/614 |
| 2002/0152796 A1* | 10/2002 | Katayama | ......... | A63B 69/3605 73/11.01 |
| 2004/0032970 A1* | 2/2004 | Kiraly | ......... | A63B 24/0021 382/103 |
| 2004/0185952 A1 | 9/2004 | Marshall | | |
| 2006/0192852 A1* | 8/2006 | Rosenthal | ......... | G06F 3/0346 348/61 |
| 2007/0026975 A1* | 2/2007 | Marty | ......... | A63B 71/0605 473/467 |
| 2007/0075891 A1* | 4/2007 | Sajima | ......... | A63B 24/0021 342/107 |
| 2008/0136907 A1 | 6/2008 | Karikko et al. | | |
| 2010/0210377 A1* | 8/2010 | Lock | ......... | A63B 69/3658 473/409 |
| 2011/0292203 A1* | 12/2011 | Kim | ......... | A63B 69/3658 348/135 |
| 2012/0196693 A1 | 8/2012 | Taksugi | | |
| 2013/0002794 A1* | 1/2013 | Hines | ......... | H04N 13/167 348/E7.078 |
| 2013/0172095 A1* | 7/2013 | Kimizuka | ......... | G06T 7/73 473/222 |
| 2013/0278727 A1* | 10/2013 | Tamir | ......... | H04N 13/239 348/47 |
| 2014/0235304 A1* | 8/2014 | Suk | ......... | A63F 13/80 463/3 |
| 2014/0277636 A1* | 9/2014 | Thurman | ......... | A63B 69/0002 700/91 |
| 2014/0379294 A1 | 12/2014 | Shubuya et al. | | |
| 2015/0029341 A1* | 1/2015 | Sinha | ......... | H04N 21/42202 348/157 |
| 2015/0318015 A1* | 11/2015 | Bose | ......... | G08B 21/043 386/248 |
| 2015/0328516 A1* | 11/2015 | Coza | ......... | A63B 71/0619 700/91 |
| 2016/0151696 A1 | 6/2016 | Chen et al. | | |
| 2016/0328839 A1 | 11/2016 | Aoki et al. | | |
| 2017/0001071 A1* | 1/2017 | Sinha | ......... | H04N 21/4223 |
| 2017/0007902 A1* | 1/2017 | Cottam | ......... | G16H 40/63 |

FOREIGN PATENT DOCUMENTS

| | | |
|---|---|---|
| CN | 104888441 A | 9/2015 |
| CN | 105641897 A | 6/2016 |
| CN | 105828893 A | 8/2016 |
| DE | 102011078772 A1 | 1/2013 |
| WO | 2000044450 A | 8/2000 |
| WO | 2001041884 A1 | 6/2001 |
| WO | 2009039367 A1 | 3/2009 |
| WO | 2014005561 A1 | 1/2014 |
| WO | 2015081303 A1 | 6/2015 |
| WO | 2016005921 A1 | 1/2016 |

\* cited by examiner a. Four-seam fastball     b. Curveball

DETECTION SYSTEMS AND METHODS

TECHNICAL FIELD

This present disclosure generally relates to a detection system, use of the detection system for analyzing an object and/or a player of a game, a method for tracking a moving object as well as a method for calculating the performance measure of a player of a game.

BACKGROUND

Object recognition solutions using computer vision are used in several industries. When tracking the state of moving objects, the precision can be measured in time resolution and precise location estimation at the same time. Both of these abilities rely in particular on computation resources and data transport capabilities of the system, as well as on the hardware used in the imaging devices. Significant entering costs of high-performance equipment are inhibitive of adapting new solutions by mainstream facilities. For spatiotemporal tracking, the limiting factors of the precision are relative speed of change and relative physical size of an object as compared to the field to be covered. For example for a camera, these factors translate into the field of view and the distance from the object, image quality and resolution, and the time resolution of recording. Ultra-high-speed (UHS) cameras are available, but at very high prices. Furthermore, transport of measured data is limited.

In the case of sport analytics, object tracking may provide information for quantitative and comparative analysis, for reconstruction or even for prediction of events. Analyzing and optimizing the performance of players, matches, techniques, etc., have been gaining growing interest. Players, trainers or audiences and even amateur consumers demonstrate high interest in, for example, automated training sessions, interactive or cyber-physical and augmented reality games, spectator-engaging sport events, virtual races against historic recordings, etc. The focus of analytics has primarily been measuring the state and performance of players. In some cases, specialized UHS and high-resolution cameras have been used, but only for a limited use, such as checking if the ball stays within the limits of the playing field. In other cases, for example football, the ball may be large enough to place sensors in it without changing its properties.

Prior art can be found in, for example, US 2004/0185952 A1 which generally relates to game ball monitoring method and apparatus, WO 2014/005561 A1 which generally relates to an equipment using cameras for recording and displaying the impact of a ball around the lines of the playing area, US 2015/0328516 A1 which generally relates to sports ball athletic activity monitoring methods and systems, WO 01/41884 A1 which generally relates to video processor systems for ball tracking in ball games, WO 2015/081303 A1 which generally relates to automated video tagging with aggregated performance metrics, U.S. Pat. No. 7,854,669 B2 which generally relates to a trajectory detection and feedback system, DE 10 2011 078 772 A1 which generally relates to a method for triggering an imaging device, and WO 2016/005921 A1 which generally relates to a visual training system and a method thereof.

However, there are scenarios in which speed and precision may both be equally important factors of performance and precise measurements may be necessary for a correct assessment of player performance.

SUMMARY

It is therefore an object of the present disclosure to provide a more precise detection system for tracking a moving object.

According to a first aspect of the present disclosure, there is provided a detection system comprising a sensor for sensing an event, and a trigger detection module coupled to the sensor, wherein the trigger detection module is configured to identify such an event sensed by the sensor to be a trigger event. The detection system further comprises an imaging device for imaging the trajectory of an object, as well as imaging device control circuitry for controlling the imaging device. The imaging device control circuitry is coupled to the trigger detection module, wherein the imaging device control circuitry is configured to control the imaging device in response to a trigger event being identified by the trigger detection module. An imaging device output of the imaging device is coupled to an imaging device control circuitry input of the imaging device control circuitry such that a feedback may be provided from the imaging device to the imaging device control circuitry. Controlling of the imaging device by the imaging device control circuitry is responsive to the feedback.

In a variant of the detection system, the imaging device control circuitry is further configured to correlate the feedback with the trigger event, and control the imaging device based on the correlation.

In a further variant of the detection system, the correlation is based on one or more of an event type, a location and a timing corresponding to the tracked moving object.

In a variant, the detection system further comprises correlation machine learning circuitry coupled to the imaging device control circuitry, wherein the correlation machine learning circuitry is configured to identify one or more characteristic properties and/or one or more patterns of the correlation, and wherein the imaging device control circuitry is further configured to control the imaging device based on the identified one or more characteristic properties and/or one or more patterns of the correlation.

In a variant, the detection system further comprises feedback machine learning circuitry coupled to the imaging device control circuitry, wherein the feedback machine learning circuitry is configured to identify one or more characteristic properties and/or one or more patterns of the feedback, and wherein the imaging device control circuitry is further configured to control the imaging device based on the identified one or more characteristic properties and/or one or more patterns of the feedback.

It will be understood that the correlation machine learning circuitry and the feedback machine learning circuitry may be integral to a single unit.

In a variant, the detection system further comprises trigger database storage circuitry for storing trigger event data. A sensor output of the sensor may thereby be coupled to a trigger database storage circuitry input of the trigger database storage circuitry for providing the trigger event data from the sensor to the trigger database storage circuitry. A trigger database storage circuitry output of the trigger database storage circuitry may be coupled to a trigger detection module input of the trigger detection module. The identification of the trigger event by the trigger detection module may hereby comprise comparing, by the trigger detection module, first trigger event data obtained from the sensor to second trigger event data stored in the trigger database storage circuitry and obtained via the sensor at an earlier point or period in time than the first trigger event data.

It will be appreciated that, in some variants, the comparison of the first trigger event data to the second trigger event data may be performed elsewhere, i.e. not by the trigger detection module. The result of the comparison may then be used by the trigger detection module for an improved identification of an event to be a trigger event.

In a variant, the detection system further comprises historical database storage circuitry for storing the trigger event data obtained via the sensor. In this variant, a machine learning module is coupled to the historical database storage circuitry, wherein the machine learning module is configured to identify one or more characteristic properties and/or one or more patterns of the trigger events stored in the historical database storage circuitry. The machine learning module may hereby be coupled to the trigger detection module for providing information regarding the one or more identified characteristic properties and/or the one or more identified patterns to the trigger detection module. The trigger detection module may be further configured to identify a trigger event based on a comparison of the one or more identified characteristic properties and/or the one or more identified patterns with the sensed trigger event. Providing historical database storage circuitry for storing the trigger event data obtained via the sensor may, for example, enable further processing that may require long-term data traces and may enable fine-tuned pattern recognition, etc., or sharing of found patterns between separate sites.

It will be understood that two or more of the machine learning module, the feedback machine learning circuitry and the correlation machine learning circuitry may be integral to a single machine learning circuit/module.

In a further variant of the detection system, the historical database storage circuitry and the trigger database storage circuitry are integral to a single trigger event database storage circuit. It will be understood that the historical database storage circuitry and trigger database storage circuitry may be combined into a single storage unit.

In a further variant, the detection system further comprises imaging device database storage circuitry for storing one or more characteristics of the imaging device. The imaging device database storage circuitry may be coupled to the imaging device control circuitry, wherein the imaging device control circuitry may be configured to control the imaging device in response to receiving information regarding the one or more characteristics of the imaging device from the imaging device database storage circuitry.

In a further variant, the detection system further comprises player detection circuitry configured to identify a movement and/or position of the player and output movement data and/or position data based on the identification of the movement and/or position. The player detection circuitry may hereby be coupled to the imaging device control circuitry, wherein the imaging device control circuitry may further be configured to control the imaging device in response to the movement data and/or position data received at the imaging device control circuitry from the player detection circuitry.

In a further variant, the detection system further comprises player database storage circuitry coupled to the player detection circuitry. The player database storage circuitry may hereby be configured to store the movement data and/or position data for later retrieval.

In a variant of the detection system, the player database storage circuitry is coupled to the imaging device control circuitry. Controlling of the imaging device by the imaging device control circuitry may hereby be responsive to the movement data and/or position data stored in the player database storage circuitry and retrieved by the imaging device control circuitry from the player database storage circuitry.

In a variant, the detection system further comprises image database storage circuitry coupled to the imaging device. The image database storage circuitry may hereby be configured to store images, output by the imaging device, for later retrieval. Such a later retrieval of one or more images from the image database storage circuitry may be desirable in order to, for example, analyze one or more characteristics of the tracked object and/or movement data and/or position data of the player.

In a variant, the detection system further comprises object analytics circuitry coupled to the imaging device output and the imaging device control circuitry input. The object analytics circuitry may hereby be configured to analyze one or more characteristics, in particular the trajectory, of the object, and provide information regarding the analyzed one or more characteristics of the object to the imaging device control circuitry. Controlling of the imaging device by the imaging device control circuitry may be responsive to the analyzed one or more characteristics of the object.

In a variant, the detection system further comprises object characteristics database storage circuitry coupled to the imaging device control circuitry. The object characteristics database storage circuitry may hereby be configured to store the analyzed one or more characteristics of the object for later retrieval by the imaging device control circuitry. Controlling of the imaging device may be responsive to the analyzed one or more characteristics of the object retrieved by the imaging device control circuitry from the object characteristics database storage circuitry.

In a further variant, the detection system comprises a plurality of imaging devices, wherein the imaging devices are configured to record the same location for creating a series of images for later analysis and/or retrieval.

It will be understood that the plurality of imaging devices may relate to different types of imaging devices, depending on the requirements and use of the detection system.

In a further variant, the detection system comprises a plurality of sensors, wherein the detection system is configured to correlate data retrieved by the plurality of sensors.

In a variant of the detection system, the imaging device control circuitry is further configured to vary the time resolution of the imaging device. The time resolution may hereby be changed in a scenario in which a characteristic property of the object and/or the player may change while the object and/or the player is being detected/monitored.

In a further related aspect of the present disclosure, there is provided a system comprising the detection system of any of the variants as described herein, and an analytics system coupled to an output layer of the detection system. The analytics system may be configured to analyze one or more characteristics of the object. The analytics system may hereby be integrated with the detection system in a single unit, or the analytics system may be provided as a unit which is separate from the detection system. The coupling of the detection system with the analytics system may hereby be a wired coupling. Alternatively, the coupling of detection system with the analytics system may be a wireless coupling in which the detection system and the analytics system may, for example, communicate with each other over a wireless network. The skilled person will be familiar with various techniques which may be used for the detection system and the analytics system to communicate with each other in a wireless manner.

In a variant of the system, the analytics system is further configured to calculate a performance measure of a player responsive to the analysis of the one or more characteristics of the object.

In a variant of the system, the calculation of the performance measure of the player is further based on the detection of the movement and/or position of the player. In a further variant of the system, the calculation of the performance measure of the player is further based on the movement and/or the position of the player relative to the trajectory of the object.

In a variant, the system further comprises the detection system according to variants in which the detection system incorporates the player detection circuitry, wherein the analytics system is further configured to analyze the movement and/or position of the player. The performance measure of the player may thereby be calculated and, for example, correlated to the analysis of one or more characteristics of the object.

In the related aspect of the present disclosure, we describe the use of the detection system according to any of the variants described herein or the system according to any of the variants described herein for analyzing one or more of: a trajectory of an object; an impact and/or a reflection of the object on a surface; a velocity of the object; a movement of a player; a position of the player; and a movement and/or a position of the player relative to the trajectory of the object.

In a further related aspect of the present disclosure, there is provided a method for tracking a moving object. The method comprises sensing an event, identifying the sensed event to be a trigger event. Controlling an imaging device by imaging device control circuitry is performed in response to the identification of the trigger event, wherein the imaging device is configured to image a trajectory of the moving object. The method further comprises providing feedback from the imaging device to the imaging device control circuitry, wherein the controlling of the imaging device by the imaging device control circuitry is responsive to the feedback.

Variants of the method provide for the advantages outlined throughout the present disclosure with regard to the detection system, and the system comprising the detection systems and analytics system.

Variants of the method for tracking a moving object correspond to the variants of the detection system and the system comprising the detection system and analytics system as outlined above.

In a further related aspect of the present disclosure, there is provided a method for calculating the performance measure of a player of a game. The method comprises tracking a moving object according to the method as outlined above, and analyzing one or more parameters of the moving object. In variants, the one or more parameters comprise one or more of a trajectory of the object, an impact of the object on a surface, a reflection of the object on a surface and a velocity of the object. The method further comprises comparing the analyzed one or more parameters to one or more predetermined conditions to calculate the performance measure of the player of the game. In order to calculate the performance measure of the player, in some variants, it may be determined as to whether the moving object may impinge on a certain predetermined area of a surface or (consecutively) areas of multiple surfaces.

Variants of the method for calculating the performance measure of a player correspond to the variants of the detection system and the system comprising the detection system and analytics system as outlined above.

It is to be noted that any variants described herein which may allow for a more precise control of the imaging device by the imaging device control circuitry may alternatively or additionally be advantageous as the imaging device may be controlled while taking into account a predicted characteristic or property of the object, for example a predicted trajectory of the object, and/or a predicted movement and/or a predicted position of the player.

BRIEF DESCRIPTION OF THE DRAWINGS

These and other aspects of the present disclosure will now be further described, by way of example only, with reference to the accompanying figures, wherein like reference numerals refer to like parts, and in which.

DETAILED DESCRIPTION

Figure 1:
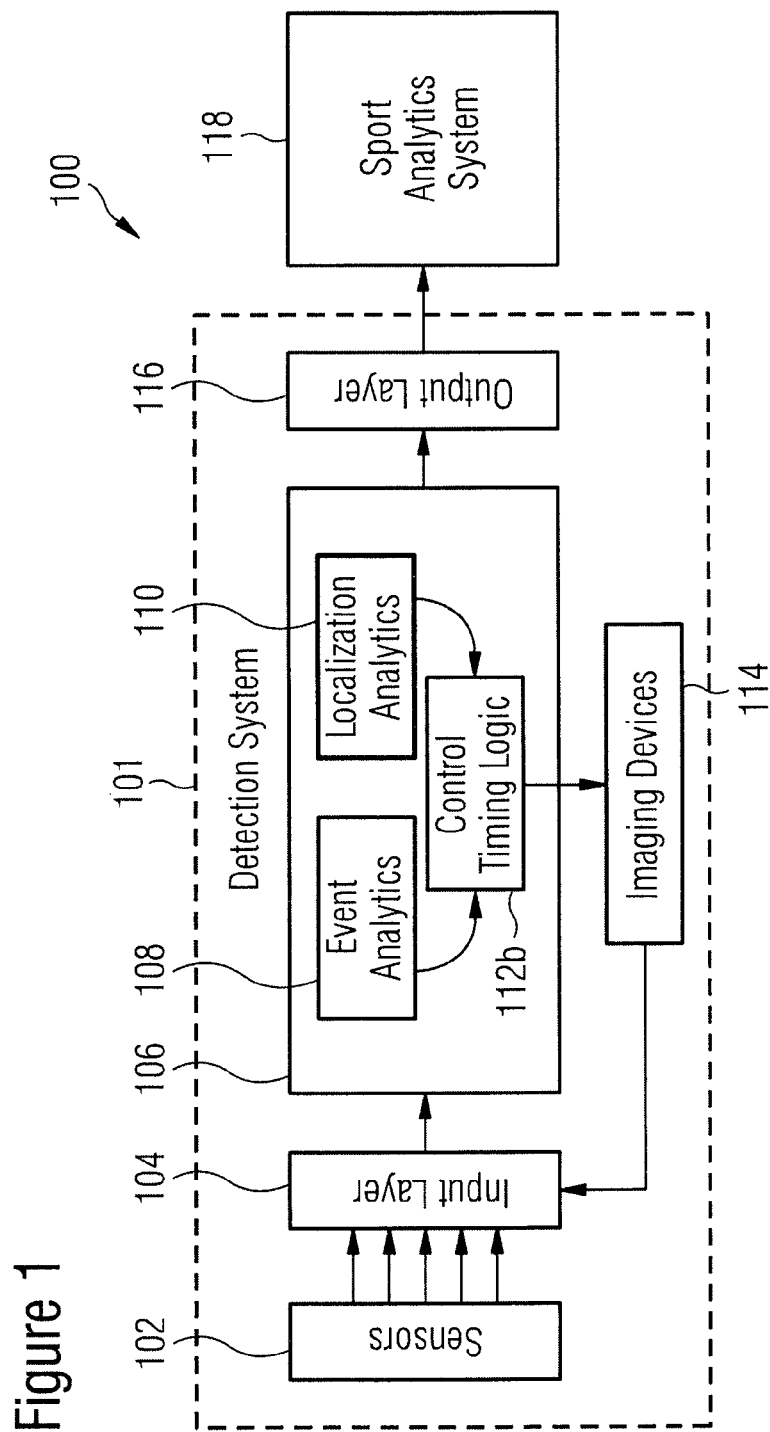
FIG. 1 shows a schematic illustration of a system according to variants of the present disclosure.

Everyday video recordings are watched in 25-30 frames per second (FPS) time-resolution, as it is generally considered to be sufficiently fast for smooth following of typical movements. In contrast, for tracking the trajectory of, for example, a ball with a spatial resolution equal to the size of the ball, the needed speed of recording may be calculated as follows: FPS=[speed of ball per sec]/[size of ball]. In the case of, for example, a baseball, using the above formula requires 40 [m/s]/0.073 [m]≈z 550 FPS. An even more extreme example is a squash game, where the ball is smaller and faster at the same time. The above formula gives: 64 [m/s]/0.04 [m]=1600 FPS.

As outlined above, variants described herein may allow for tracking an UHS object using low-speed devices. The proposed systems and methods provide for a complex optimized solution for computer-vision-based event measurements involving HS objects, such as real-time analysis for (U)HS racket sports.

Using external sensor data adaptive time resolution of recording may capitalize on inter- and intra-event characteristics. This may allow for precise measurements while minimizing the unnecessary load on the transmitting and processing units. The controlling method may also enable UHS recording using multiple low-speed devices working collaboratively. In some variants, optimization of recording, network communication and data processing in an analytics-driven control loop may be achieved by using external sensor triggers, historical databases and machine learning. As an open-ended system, it may provide event characteristics, for example, for various sport analytics platforms.

The systems and methods as described herein may provide for a three-fold optimization for real-time object detection related to events involving small HS objects. Using sensor fusion (i.e. using various devices working together in a collaborative manner) and analytics, the described methods may capitalize on i) inhomogeneous distribution of events, focusing on active time interval and location; ii) intrinsic asymmetry of event characteristics times, with adapted precision; and iii) collaborative recording, i.e., adaptive framerates and high time-resolution measurements even with low-cost devices lacking UHS capabilities.

The optimized detection using variants as described herein may allow for affordable systems for high-performance tasks to be provided. In particular, excess data load is avoided by optimization; delays which may be introduced are lower; parallel and/or multi-side setups which may be used may provide for a single cheaper infrastructure.

Variants described herein may further take advantage of cloud analytics for machine learning. Multiple locations may hereby share collected event patterns and raw sensor data. The initial learning phase may be shortened, whereby improved configurations may be shared between sites.

Variants described herein may further allow for an easy adaptation by already existing active facilities. As a result, no manufacturing may be needed, such that no delayed disturbance arises for the facility.

As the system described herein is an open system, a flexible sensor setup may be provided. The system may hereby be expandable by custom analytics solutions. Furthermore, variants described herein may allow for a wide range of use cases which may use the output of the system: from performance metrics feedback to gamification, enhanced broadcasting or social solutions.

Variants described herein relate to a detection system and related methods for real-time control of digital cameras collaborating in order to accurately detect time, location and other characteristics of events involving HS, small object(s) (for example during a squash game).

The detection system as described in variants herein may allow for precise measurements while advantageously minimizing the unnecessary load on the transmitting and processing units. Furthermore, the detection system may use event characteristics measurements, for example, for optimized detection of high-speed objects with a sensor and an imaging device which are controlled based on real-time analytics.

Variants described herein may allow for a complex analytics trigger control of an imaging device which provides a feedback to the imaging device control circuitry, such that a collaborative coupling of the various features of the detection system may achieve comparatively high time-resolution using several comparatively low-speed devices without any costly equipment.

Variants described herein may allow for an optimized adaptive timing which may follow an inhomogeneous event distribution during sessions on the one hand, and the varying intrinsic characteristic times of the specific events on the other hand.

As outlined above, in a variant of the detection system, the imaging device control circuitry may be further configured to correlate the feedback with the trigger event and control the imaging device based on the correlation. This may be particularly advantageous, as the controlling of the imaging device by the imaging device control circuitry may be improved, as the trigger event, based on which the imaging device control circuitry controls the imaging device, may be identified with higher accuracy. In some examples, a response time of the imaging device control circuitry being triggered to control the imaging device based on a trigger event being identified may be reduced, and/or the timing of the triggering may be more precise. The correlation may hereby be based on one or more of an event type, a location and a timing corresponding to the tracked moving object. This may be advantageous as the triggering of the imaging device control circuitry may be particularly precise as it may be based on a specific characteristic of the tracked moving object, which may be correlated with the trigger event. The correlation may therefore be dependent on the specific characteristic of the tracked moving object which is detected with the imaging device.

In order to allow for a more precise identification of the correlation between the feedback and the trigger event, a variant may be provided in which the detection system further comprises a correlation machine learning circuitry coupled to the imaging device control circuitry, wherein the correlation machine learning circuitry is configured to identify one or more characteristic properties and/or one or more patterns of the correlation, and wherein the imaging device control circuitry is further configured to control the imaging device based on the identified one or more characteristic properties and/or one or more patterns of the correlation. Hence, controlling the imaging device by the imaging device control circuitry may be further improved.

The detection system may comprise a feedback machine learning circuitry coupled to the imaging device control circuitry, wherein the feedback machine learning circuitry is configured to identify one or more characteristic properties and/or one or more patterns of the feedback, and wherein the imaging device control circuitry is further configured to control the imaging device based on the identified one or more characteristic properties and/or one or more patterns of the feedback. This may allow for a more precise identification of the trigger event. Hence, controlling the imaging device by the imaging device control circuitry may be further improved.

The detection system may be provided in a more compact format in a variant in which the correlation machine learning circuitry and the feedback machine learning circuitry are integral to a single unit.

In variants in which the correlation machine learning circuitry and/or the feedback machine learning circuitry are used, the triggering may be more precise based on historic datasets and/or real-time streams.

FIG. 1 shows a schematic illustration of a system 100 as described herein, and which comprises, in this example, a detection system 101 and a sport analytics system 118.

The diagram shown in FIG. 1 depicts an overall view on how the detection system may use sensor data for optimally controlling imaging devices and providing localization results and persistent recordings through an output layer. A sport analytics system may be enabled by the real-time measurements for calculating quantitative metrics and providing real-time feedback to end-users related to the specific events of interest.

In this example, the system 100 receives input information from sensors 102 through an input layer 104 combining time and location information of each measurement.

The system 100 comprises, in this example, circuitry 106 which includes an event analytics module 108, localization analytics circuitry 110 (which may be ball position analytics circuitry 110a) and control timing logic circuitry 112b. The event analytics module 108 is configured to determine triggers, while the localization analytics circuitry 110 is configured to use custom logic related to the characteristics of the event of interest. From these, the control timing logic circuitry 112b is configured to provide optimally timed commands for the imaging devices 114, which may, in some examples, be cameras 114.

Using a customizable output layer 116, all final and partial results may be shared with the external sport analytics system 118, where the location of the object and event characteristics may be used for various use cases, such as, for example, performance metrics calculations or triggering of further measurement chains.

The control timing logic circuitry 112b is configured to control the imaging devices 114, and an output of the imaging devices 114 is fed back to the circuitry 106 via the input layer 104. Controlling the imaging devices 114 by the control timing logic circuitry 112b is therefore responsive to the feedback from the imaging devices 114.

Figure 2:
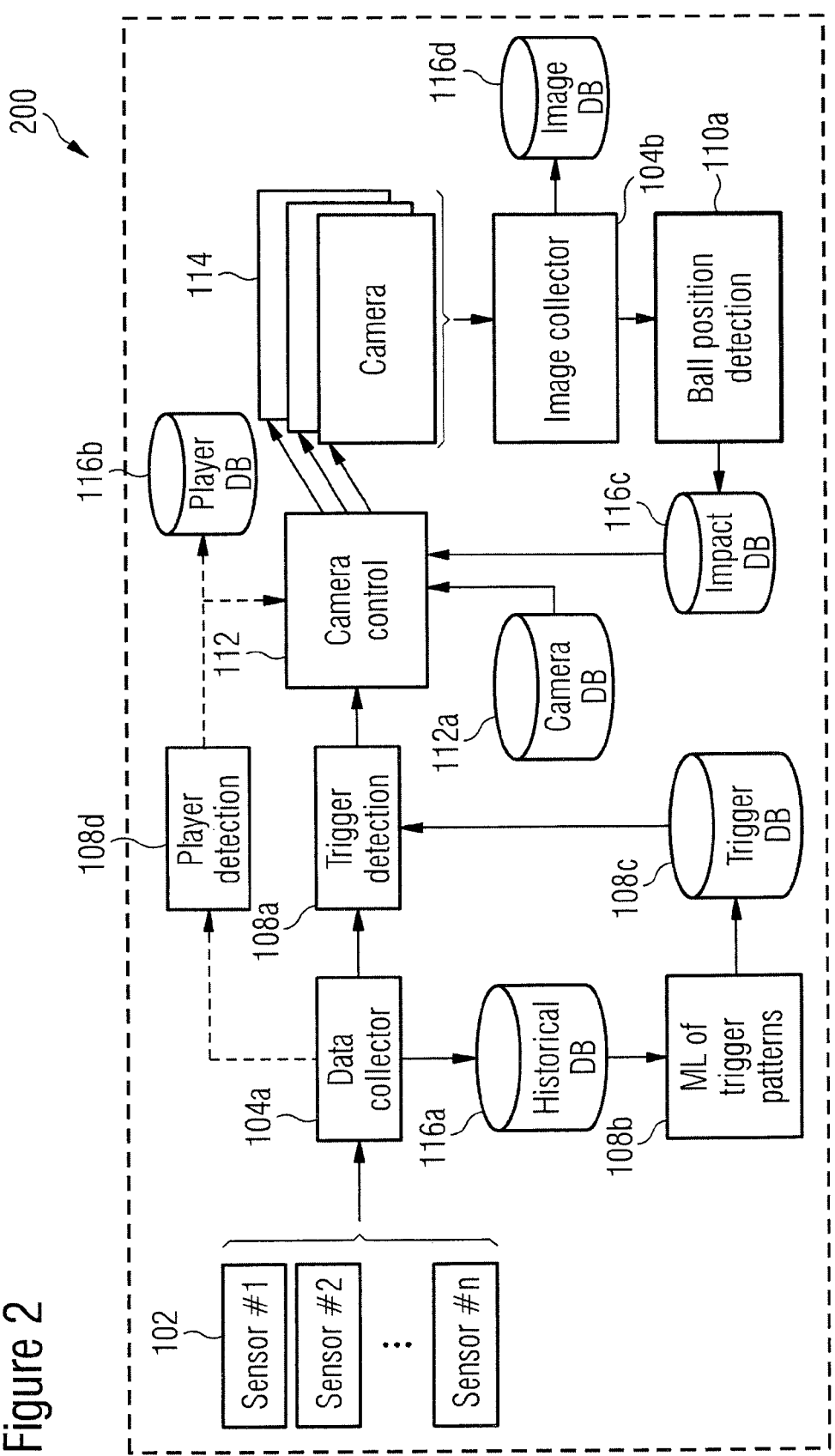
FIG. 2 shows a schematic illustration of a detection system according to variants of the present disclosure.

FIG. 2 shows a schematic illustration of the detection system 200 with color coding following the logical units of the illustration of FIG. 1.

Generally, the input layer collects sensor and camera image data with time and location information. The various modules and devices used in variants of the methods and systems as described herein are depicted in boxes, while the various persistent recordings in databases form the output layer.

In this example, n sensors 102 are provided in the detection system 200. The detection system may hereby be configured to correlate data retrieved by the plurality of sensors. This may be advantageous as such a correlation of data retrieved by the plurality of sensors may be used by the trigger detection module, thereby increasing the probability that a true trigger event is being identified by the trigger detection module.

The sensors 102 are coupled to a data collector 104a, whereby the sensors 102 of the detection system 200 serve information about the trigger event that can be used later by the system to control the camera(s) 114. Such information can be, for example, the sound of the ball hit by the racket or input from the accelerometer installed in the racket. It will be understood that the sensors 102 may alternatively or additionally be light sensors, IR sensors, ultrasonic sensors, touch sensors, proximity sensors, pressure sensors, level sensors, or other types of sensors. It will further be appreciated that the sensors 102 may in fact be different sensors, whereby some of the sensors 102 may be a different type (or types) of sensor(s) compared to other types of sensors 102.

The input events sensed by the sensors 102 are collected by the data collector 104a component which is part of the input layer 104 of the detection system 101.

In this example, the data collector 104a stores all input data in the historical database storage circuitry 116a to enable further processing that may require long-term data traces and may enable fine-tuned pattern recognition, etc., or sharing of found patterns between separate sites.

In the example detection system 200 shown in FIG. 2, the historical database storage circuitry 116a is coupled to a machine learning module 108b which uses the historical database storage circuitry 116a and identifies characteristic properties and patterns of the trigger events.

As outlined above, according to some examples, the detection system further comprises a historical database storage circuitry for storing the trigger event data obtained via the sensor. A machine learning module may be coupled to the historical database storage circuitry, wherein the machine learning module is configured to identify one or more characteristic properties and/or one or more patterns of the trigger events stored in the historical database storage circuitry. The machine learning module may hereby be coupled to the trigger detection module for providing information regarding the one or more identified characteristic properties and/or the one or more identified patterns to the trigger detection module. The trigger detection module may be further configured to identify a trigger event based on a comparison of the one or more identified characteristic properties and/or the one or more identified patterns with the sensed trigger event. Providing a historical database storage circuitry for storing the trigger event data obtained via the sensor may, for example, enable further processing that may require long-term data traces and may enable fine-tuned pattern recognition, etc., or sharing of found patterns between separate sites. The machine learning module may hereby advantageously identify the characteristic properties and/or patterns of the trigger events. The identification of a trigger event by the trigger detection module may therefore be even more precise, as it may be based on a comparison of event data obtained via an event sensed by the sensor with characteristic properties and/or patterns identified by the machine learning module.

Inferred knowledge obtained via the machine learning module 108b is stored, in this example, in the trigger database storage circuitry 108c. In this example, both databases are part of the output layer 116 shown in FIG. 1.

As outlined above, in some examples, the detection system further comprises trigger database storage circuitry for storing trigger event data. A sensor output of the sensor may thereby be coupled to trigger database storage circuitry input of the trigger database storage circuitry for providing the trigger event data from the sensor to the trigger database storage circuitry. A trigger database storage circuitry output of the trigger database storage circuitry may be coupled to a trigger detection module input of the trigger detection module. The identification of the trigger event by the trigger detection module may hereby comprise comparing, by the trigger detection module, first trigger event data obtained from the sensor to second trigger event data stored in the trigger database storage circuitry and obtained via the sensor at an earlier point or period in time than the first trigger event data. This may provide for an improved identification of a trigger event by the trigger detection module, as a comparison may be made between event data obtained via an event sensed by the sensor and event data obtained previously. As a result, the identification of the trigger event by the trigger detection module may be more precise, such that, for example, false identifications of a trigger event by the trigger detection module may be minimized or even prevented.

The trigger database storage circuitry 108c is coupled to the trigger detection module 108a. The trigger detection module 108a is further coupled to the data collector 104a which forwards the raw input data to the trigger detection module 108a. The trigger detection module 108a then identifies the trigger event and calculates its characteristic parameters. The previously inferred trigger patterns obtained via the machine learning module 108b are used, in this example, in the detection process as well.

In a variant of the detection system, the historical database storage circuitry and the trigger database storage circuitry are integral to a single trigger event database storage unit. It will be understood that the historical database storage circuitry and trigger database storage circuitry may be combined into a single storage unit, thereby allowing for a more simple structure and configuration of the detection system.

The identified trigger event and all of its properties are then used by the imaging device control circuitry 112, which is, in this example, camera control circuitry 112. The camera control circuitry 112 is in charge of controlling all the imaging equipment, which includes, in this example, a plurality of cameras 114.

In this example, the camera control circuitry 112 takes into account the camera specific (configuration) information from the imaging device database storage circuitry 112a (which is, in this example, camera database storage circuitry 112a) to which the camera control circuitry 112 is coupled.

Furthermore, in this example, player detection circuitry 108d is coupled between the data collector 104a and the camera control circuitry 112. The player detection circuitry 108d is configured to identify the movement and/or position of the player or players. The player detection circuitry 108d is coupled to the player database storage circuitry 116b in which the results of the identification of the movement and/or position of the player or players are stored.

As can be seen from FIG. 2, the camera control circuitry 112 is coupled to the trigger detection module 108a, such that the camera control circuitry 112 controls the plurality of cameras 114 in response to a trigger event being identified by the trigger detection module 108a.

The camera control circuitry 112, when controlling the plurality of cameras 114, therefore takes into account the camera specific (configuration) information from the camera database storage circuitry 112a, the identified trigger event received from the trigger detection module 108a and the movement and/or position of the player or players identified by the player detection circuitry 108d that stores its results in the player database storage circuitry 116b. The result of the computation is then used to optimally control the cameras 114.

The camera control circuitry 112 is, in this example, further configured to retrieve data from the player database storage circuitry 116b which may be taken into account by the camera control circuitry 112 when controlling the cameras 114. Variants of the detection system may therefore advantageously allow for analyzing the movement and/or position of the player, in particular with respect to, for example, a trajectory of an object, in order to determine a performance measure of the player.

Variants which provide for a player database storage circuitry coupled to the player detection circuitry may be advantageous as they may allow for accessing movement data and/or position data from the player database storage circuitry in order to calculate, for example, a performance measure of the player.

As outlined above, controlling of the imaging device by the imaging device control circuitry may hereby be responsive to the movement data and/or position data stored in the player database storage circuitry and retrieved by the imaging device control circuitry from the player database storage circuitry. This may be particularly advantageous as the imaging device control circuitry may access the player database storage circuitry in order to optimize controlling the imaging device based on historical movement data and/or position data stored in the player database storage circuitry. It will be understood that this may be particularly desirable in a scenario in which one or more imaging devices may generally be configured to track the player, allowing for improving obtaining movement data and/or position data of the player.

The images captured by the cameras 114 are, in this example, collected by the image collector 104b (another part of the input layer 104 as shown in FIG. 1). The captured images are stored in the image database storage circuitry 116d and further forwarded to the ball position analytics circuitry 110a.

In some examples, the detection system comprises imaging device database storage circuitry for storing one or more characteristics of the imaging device. The imaging device database storage circuitry may be coupled to the imaging device control circuitry, wherein the imaging device control circuitry may be configured to control the imaging device in response to receiving information regarding the one or more characteristics of the imaging device from the imaging device database storage circuitry. This may be particularly advantageous as controlling the imaging device by the imaging device control circuitry may be optimized as the specifications and capabilities of the imaging device may be taken into account when controlling the imaging device.

In this example, multiple cameras are oriented to record the same location in order to create an ordered series of images using timestamps and other parameters for further analysis.

The ball position analytics circuitry 110a is configured, in this example, to calculate all the parameters of the impact of the ball on the wall (timestamp, angle, speed) as well as the trajectory of the ball. The results of the calculation of the ball position analytics circuitry 110a are then stored in the impact database storage circuitry 116c. The impact database storage circuitry 116c serves as the input for feedback to the camera control circuitry 112 in order to fine-tune its further decisions based on the previous events.

As outlined above, controlling of the imaging device may be responsive to the analyzed one or more characteristics of the object retrieved by the imaging device control circuitry from the object characteristics database storage circuitry. This may be particularly advantageous as controlling the imaging device by the imaging device control circuitry may be even more precise as the determination as to how the imaging device is to be controlled may further be based on data about one or more characteristics of the object obtained previously.

Furthermore, controlling of the imaging device by the imaging device control circuitry may be responsive to the analyzed one or more characteristics of the object. This may allow for an even more precise control of the imaging device by the imaging device control circuitry, in particular as the one or more characteristics of the object may be taken into account when determining as to how the imaging device is to be controlled.

In this example, all the databases proposed in the system 200 serve as the output layer of the detection system, and these are the places where any additional analytics component can access the raw measurements or partial analytical results and query detailed information about the identified trigger, the inferred position and movement of the player or players, the board trajectory and its impact on the wall.

It will be understood that the system 200 as shown in FIG. 2 is merely an explanatory illustration of a preferred detection system. It will be appreciated that many of the components of the detection system 200 are merely optional, and the detection system in one of its basic forms may be implemented using only some of the components as shown in FIG. 2. In particular, in some variants, one or more sensors 102, the trigger detection module 108a, the camera control circuitry 112 as well as one or more cameras 114 (or one or more other imaging devices) may be used, in which a feedback from the one or more cameras 114 to the camera control circuitry 112 is provided.

Furthermore, it will be understood that the one or more cameras 114 may be configured to alternatively or additionally record videos, rather than being configured to take images only.

Furthermore, in some variants, detection system comprises a plurality of imaging devices, wherein the imaging devices are configured to record the same location for creating a series of images for later analysis and/or retrieval. This may be particularly advantageous as a series of images created by a plurality of imaging devices may allow for a more precise analysis of the object and/or the player. The plurality of imaging devices may hereby work together in a collaborative manner.

The systems and methods described herein may be used in support analytics scenarios. The approach may be needed in situations where speed and precision together contribute to high performance, and quantitative measures may only be calculated with capturing of relevant changes during specific events. It will be understood that the collaborative recording optimized by external events may also be used in other fields (for example industrial measurements).

Each of the following examples may be realized by a) using UHS cameras, or by b) replacing each UHS camera by a multi-camera setup. In the latter case, a series of images coming from the multi-camera unit may be arranged by the collector to perform a stream similar to what a single UHS camera may provide.

Furthermore, each of the following examples may have a) a single playing field, or b) multiple similar playing fields with their respective sensors setups. For both cases, a single central analytics system, either at the support facility or at a remote location, may use learning from the unified historic datasets.

Figure 3:
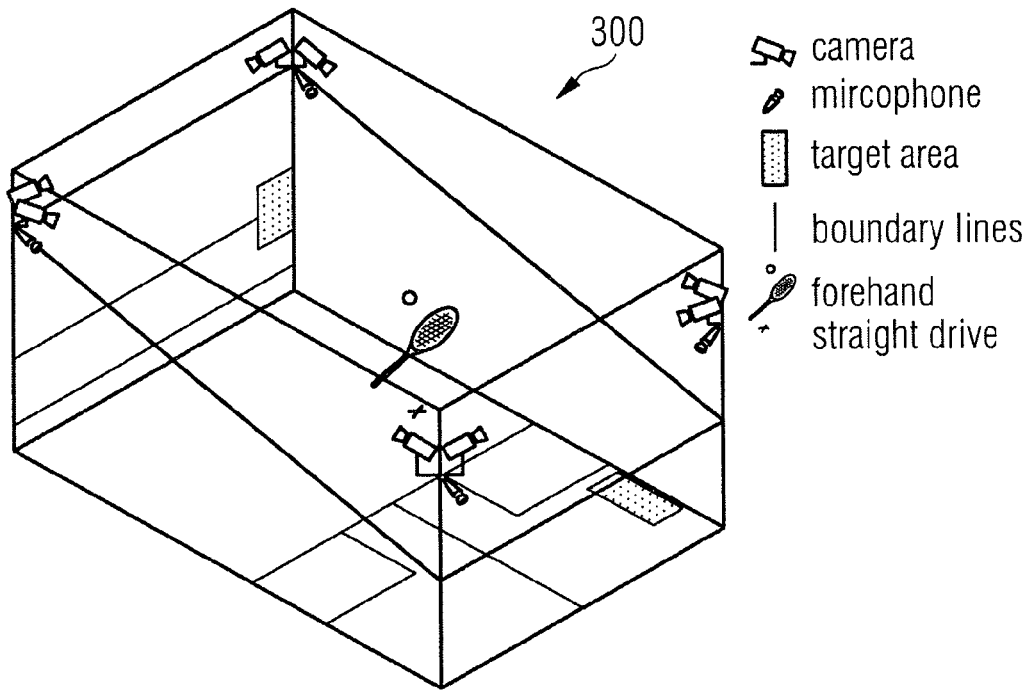
FIG. 3 shows a schematic illustration of an implementation of the system according to variants of the present disclosure.

FIG. 3 shows a schematic illustration 300 of an implementation of the system according to examples as described herein. In this scenario, real-time detection of the parameters of the ball impact event (time, location, player ID) on the main wall is provided during a squash session.

In this example, cameras record the main and side walls as well as the players. Microphones capture audio recording and are used in this example with racket sensors for triggering event analytics. An 'X' indicates the current position of the player. The corresponding optimal target area calculated by the sport analytics system is highlighted as a rectangular area on the main wall. Hitting the optimal target area may ensure reaching an optimal, highlighted landing area on the floor (indicated in this example by a rectangular area on the right hand side of the floor).

The sport analytics system may use the detected ball impact location on the wall to calculate a performance measure of the player, which may also depend on information regarding the player position.

The detection system may serve for the support analytics system as input for real-time feedback of performance metrics for one or more players and/or trainers. In one example, the player may have to practice precisely hitting a specific area on the wall. Another example may be related game performance metrics, as illustrated in FIG. 3. The system may be used to quantify as to how well the player can target the optimal area dependent on his or her position that would send the ball to the location which may be the most difficult to reach for the other player.

UHS recording may be needed, but event distribution during a session may be sparse and uneven. Thus constant measurements may create unnecessary data load without analytical value for this use case, and the systems and methods described herein may result in significant optimization.

In this example, player detection and ball impact detection use separately controlled cameras. Furthermore, in this example, racket and audio sensors complement the measurements. A machine learning module is used in this example which may find one or more trigger patterns in raw datasets.

As the various sensors shown in FIG. 3 may work together in a collaborative manner, this sensor fusion may result in higher precision, thereby resulting in a reduction of false trigger events being identified by the trigger detection module.

Figure 4:
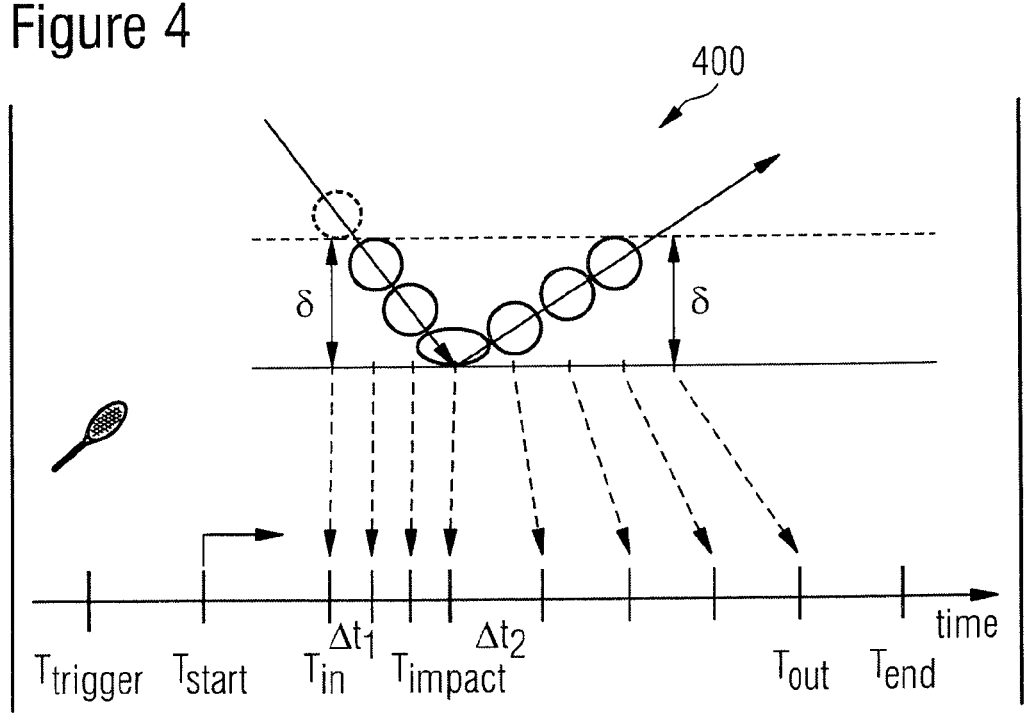
FIG. 4 shows a schematic illustration of a scenario in which the detection system according to variants of the present disclosure is used.

FIG. 4 shows a further schematic illustration 400 of a scenario in which the detection system as described herein may be used.

In this example, real-time detection of the intrinsic parameters of the ball impact events (incoming/outgoing speeds, directions, position) on the main wall is provided during a squash session.

As the restitution coefficient (which is defined by the ratio between the relative velocity after the collision and the relative velocity before the collision) of the squash ball is significantly lower than 1 by design, it will inevitably slow down after high-energy impact. The restitution coefficient of the ball may also be dependent on the temperature, etc., and may vary between balls and during the game. In order to measure event parameters, precise recording in the vicinity of the ball may be needed. Varying the speed of recording may hence be required during the event. Adapting the frame rates may optimally require both collaborative recording for UHS time resolution and flexible control.

The imaging device control circuitry may, in some examples, be further configured to vary the time resolution of the imaging device. This may be particularly advantageous in a scenario in which a characteristic property of the object and/or the player may change while the object and/or the player is being detected/monitored.

The schematic illustration shown in FIG. 4 may depict elements of the example implementation of the methods and systems as described herein and as shown in FIG. 2.

The incoming ball hits the wall at the time $T_{impact}$. The velocity of the ball after the impact is significantly lower compared to the velocity of the ball before the impact. The angle of reflection of the ball trajectory when measured from the wall is, in this example, smaller compared to the angle of incidence of the ball before the ball hits the wall.

$T_{trigger}$ denotes the time at which the trigger event is being identified such that the imaging devices are being controlled from the time $T_{start}$ onwards. In this example, there is a delay between a trigger event being identified at the time $T_{trigger}$ and the time $T_{start}$ from which time onwards the imaging devices are being controlled. However, it will be understood that there may not be a delay between the times $T_{trigger}$ and $T_{start}$.

In this example, an active interval follows a trigger event of the racket hit and $T_{start}$ and Tend are progressively adapted to the minimum required distance (δ) from the wall for precise trajectory estimates. Tin hereby denotes the starting time at which the ball is within the minimum required distance (δ) before the ball hits the wall, and Tout denotes the last point in time at which the ball is still within the minimum required distance (δ) after the ball has hit the wall before the ball is further away from the wall than the minimum required distance (δ).

In this example, the time resolution of the camera or cameras is varied (from $\Delta t_1$ to $\Delta t_2$) in view of the coefficient of restitution of the ball being lower than 1. As outlined above, this may provide for an optimized tracking of the trajectory of the ball as the velocity of the ball changes after the ball has hit the wall.

Figure 5A:
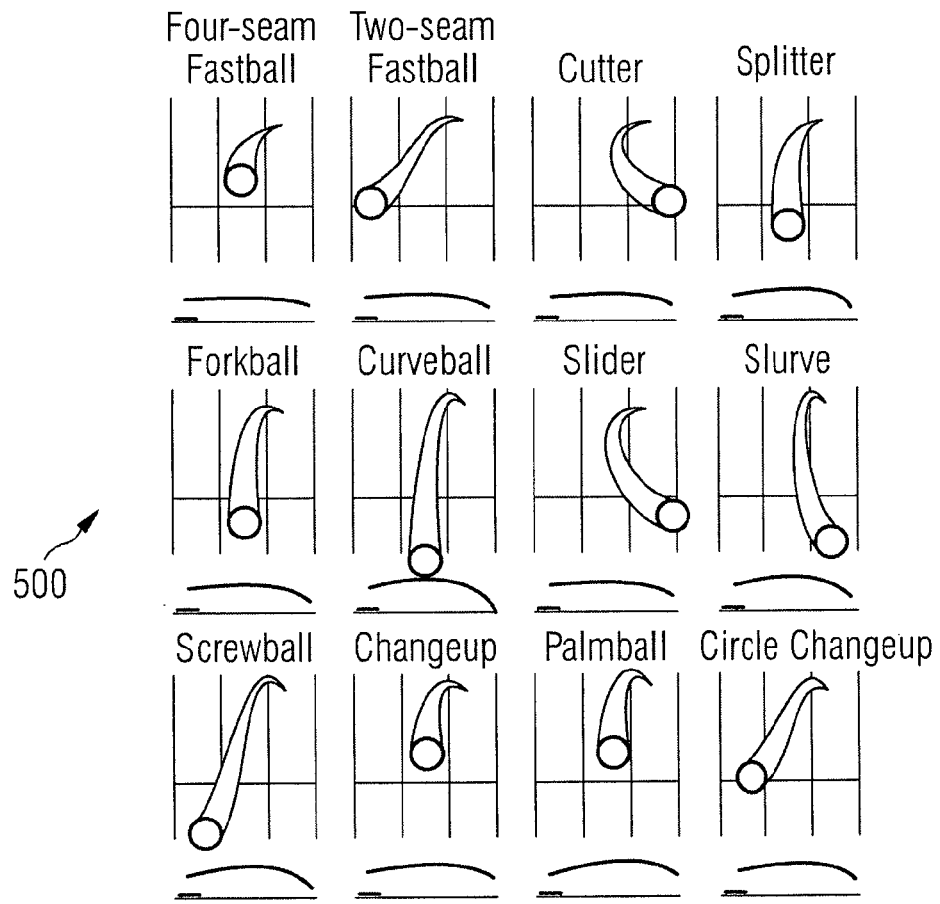
FIGS. 5a and b show an example in which the system according to variants of the present disclosure can be implemented.

FIGS. 5a and b show an example in which variants of the methods and systems as described herein may be implemented.

FIG. 5a, taken from www.lokeshdhakar.com, depicts types of pitches as seen from the point of view of the catcher of a baseball game. The upper panels indicate the trajectory of the ball as seen from the arrival point. The lower panels show the corresponding vertical trajectories of the ball from the pitcher location to the catcher location.

Figure 5B:
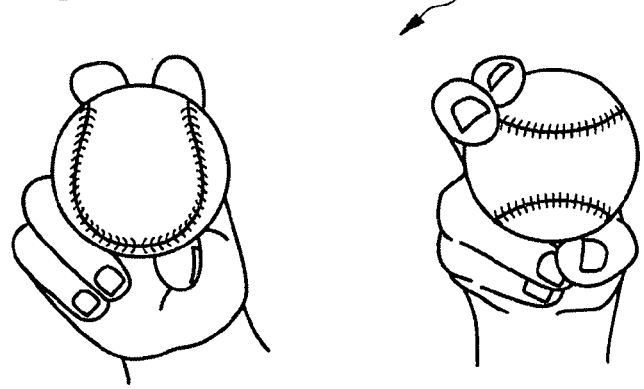

FIG. 5b shows two different grip types corresponding to the four-seam fastball and the curveball pitches, respectively.

Variants of methods and systems as described herein may therefore provide for real-time detection of the intrinsic parameters of the pitching and catching events during a baseball session.

The performance metrics of a pitcher and a batter (i.e. the throwing and receiving players) may use details of the ball tracking results. As the events of interest are, in this example, the pitching and catching, optimization may avoid excessive data load, by using external triggers. As the ball may be very fast (see above), spatial precision may require UHS recording as well.

In this example, the logic has three steps: i) the start of recording for the pitching event is triggered by the pitcher's leg position; ii) the grip type is being determined; iii) from the grip type, the typical time-of-flight can be calculated based on trajectory patterns, and the recording at the receiver side is triggered.

Failed pitches may also be detected by using one or more parallel plane(s) of detection perpendicular to the line connecting the pitcher and batter locations when determining the trajectory of the incoming ball. During a baseball game, pitching may have basic types which may be determined by the grip on the ball and the consequent trajectory pattern. For example, about 70% of pitches are of the type called 'four-seam fastball' (see FIG. 5b).

Figure 6:
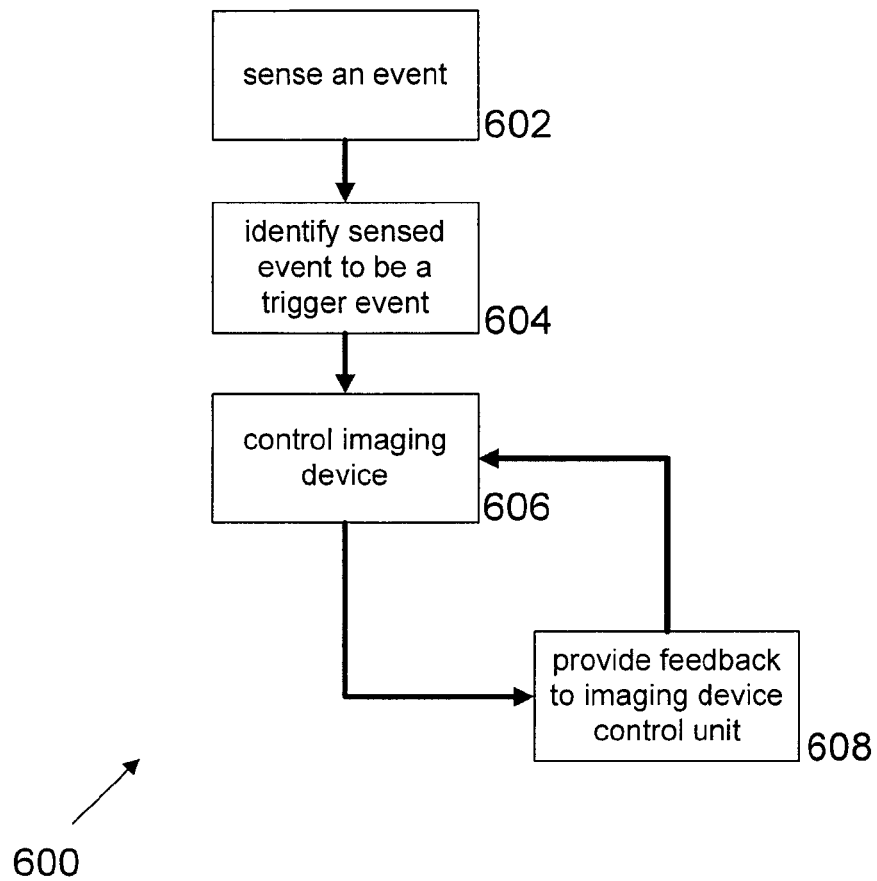
FIG. 6 shows a schematic block-diagram of a method according to variants of the present disclosure.

FIG. 6 shows a schematic block-diagram of a method 600 according to example implementations as described herein.

At step 602, an event is being sensed. At step 604, the sensed event is being identified as a trigger event. In response to the identification of the sensed event being a trigger event, an imaging device is controlled at step 606. At step 608, the imaging device provides a feedback to the imaging device control circuitry which may then be able to optimize controlling of the imaging device.

Figure 7:
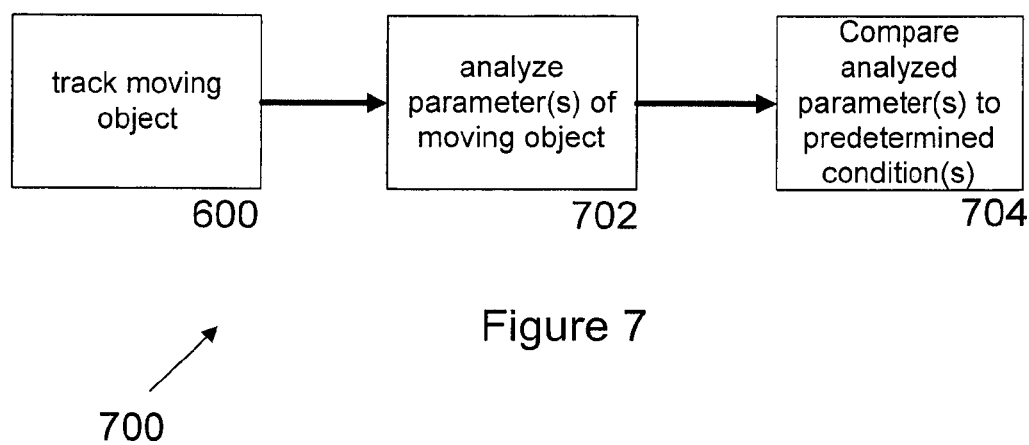
FIG. 7 shows a schematic block-diagram of a further method according to variants of the present disclosure.

FIG. 7 shows a schematic block-diagram of a further method 700 according to example implementations as described herein.

In this example, a moving object is being tracked at step 600 using the method as depicted in FIG. 6. At step 702, one or more parameters of the moving object are analyzed using variants of the system as described herein. These parameters include, but are not limited to a trajectory of the object, and impact of the object on a surface, a reflection of the object on a surface and/or a velocity of the object.

At step 704, the analyzed one or more parameters are then compared to one or more predetermined conditions in order to calculate the performance measure of the player of the game.

As outlined above, in variants the analytics system is further configured to calculate a performance measure of a player responsive to the analysis of the one or more characteristics of the object. This may be particularly advantageous as the performance measure of the player may be measured and improved on the basis of a detailed analysis of the one or more characteristics of the object.

The performance of the player may be improved using variants of the system in which the calculation of the performance measure of the player is further based on the detection of the movement and/or position of the player. An even more precise calculation of the performance measure of the player may be achieved by correlating the movement and/or the position of the player with the trajectory of the object.

Figure 8:
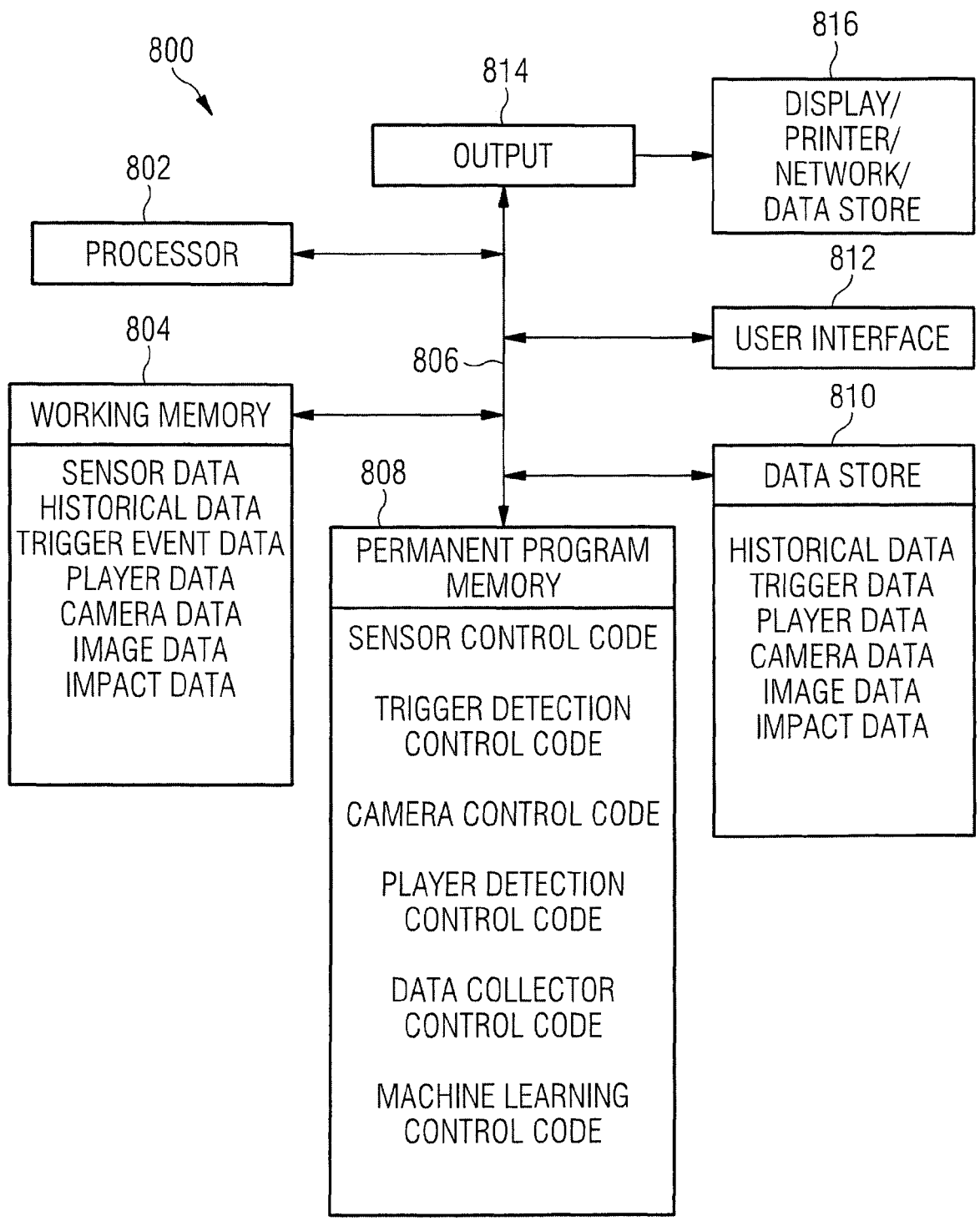
FIG. 8 shows a schematic block-diagram of a system according to variants of the present disclosure.

FIG. 8 shows a schematic block-diagram of a system 800 according to examples as described herein.

Broadly speaking, the system 800 comprises a suitably programmed general purpose processor 802. The system 800 comprises processor 802, working memory 804, permanent program memory 808, and a data store 810 all linked by a common data line (bus) 806. In this example, a user interface 812 is also provided for configuring the system 800. User interface 812 can also be used as an input to receive, for example, one or more of historical data, trigger data, player data, camera data, image data and impact data. The system 800 also includes an output 814 connected to one or more of a display, a memory, a printer, a data store and a network (for example a cloud) 816 in order to display, store, print or distribute, for example, any one or more of historical data, trigger data, player data, camera data, image data and impact data.

The skilled person will appreciate that additionally or alternatively other forms of storage/output may be employed.

In this example, working memory 804 is used for holding (which may be transient), processing and manipulating sensor data, historical data, trigger event data, player data, camera data, image data and impact data.

Permanent program memory 808 stores operating system code (which can be platform independent) comprising (optional) user interface code, operating system code, sensor control code for controlling one or more sensors, trigger detection control code for controlling the trigger detection module, camera control code for controlling the one or more cameras, player detection control code for detecting the one or more players, data collector control code for controlling the data collector to receive data from the one or more sensors, and machine learning control code for controlling the machine learning module.

These codes are loaded and implemented by processor 802 to provide corresponding functions for the system 800.

Some or all of these codes may be provided on a carrier medium, which may be a removable storage medium, for example a CD-ROM.

Data store 810 stores historical data indicative of characteristics or patterns of trigger event data obtained via the one or more sensors, trigger data obtained via the one or more sensors, player data indicative of a movement and/or position of one or more players, camera data indicative of one or more properties/capabilities of the one or more cameras (or generally imaging devices), image data relating to images taken of a moving object which may then be used to obtain information regarding the trajectory of the object, and impact data indicative of an impact of the moving object on a surface (such as, but not limited to the velocity of the object before its impact on the surface, the velocity of the object after its impact on the surface, an angle of incidence and an angle of reflection).

The present disclosure further provides processor control code to implement the above-described systems and methods, for example on a general purpose computer system or on a digital signal processor (DSP). The code is provided on a non-transitory physical data carrier such as a disk, CD- or DVD-ROM, programmed memory such as non-volatile memory (e.g. Flash) or read-only memory (Firmware). Code (and/or data) to implement variants of the present disclosure may comprise source, object or executable code in a conventional programming language (interpreted or compiled) such as C, or assembly code, or code for a hardware description language. As the skilled person will appreciate, such cold and/or data may be distributed between a plurality of coupled components in communication with one another.

Figure 9:
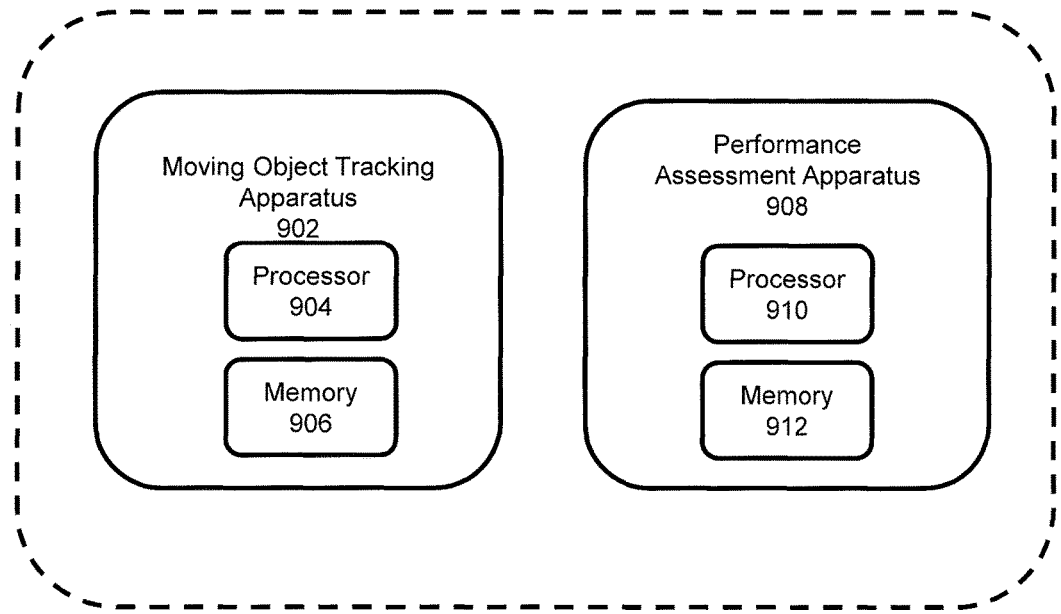
FIG. 9 shows a schematic block-diagram of a moving object tracking apparatus and a performance assessment apparatus according to variants of the present disclosure.

In order to realize the above and further functionalities regarding the tracking of a moving object, a moving object tracking apparatus 902 is provided in embodiments, as shown in FIG. 9.

The moving object tracking apparatus 902 comprises a processor 904 and a memory 906. The memory 906 is coupled to the processor 904 and comprises program code portions that allow tracking a moving object according to embodiments as described herein upon executing the program code portions.

Furthermore, in order to realize the above and further functionalities regarding the calculation of the performance measure of a player of a game, a performance assessment apparatus 908 is provided in embodiments, as shown in FIG. 9.

The performance assessment apparatus 908 comprises a processor 910 and a memory 912. The memory 912 is coupled to the processor 910 and comprises program code portions that allow calculating the performance measure of a player of a game according to embodiments as described herein upon executing the program code portions.

The moving object tracking apparatus 902 and the performance assessment apparatus 908 are shown in FIG. 9 as a single unit. It will however be appreciated that the moving object tracking apparatus 902 and the performance assessment apparatus 908 may be provided in separate units. Alternative the moving object tracking apparatus 902 and the performance assessment apparatus 908 may be combined in a single apparatus, in which the processor 904 and processor 910 are integral to a single processor, and the memory 906 and the memory 912 are integral to a single memory.

Figure 10:
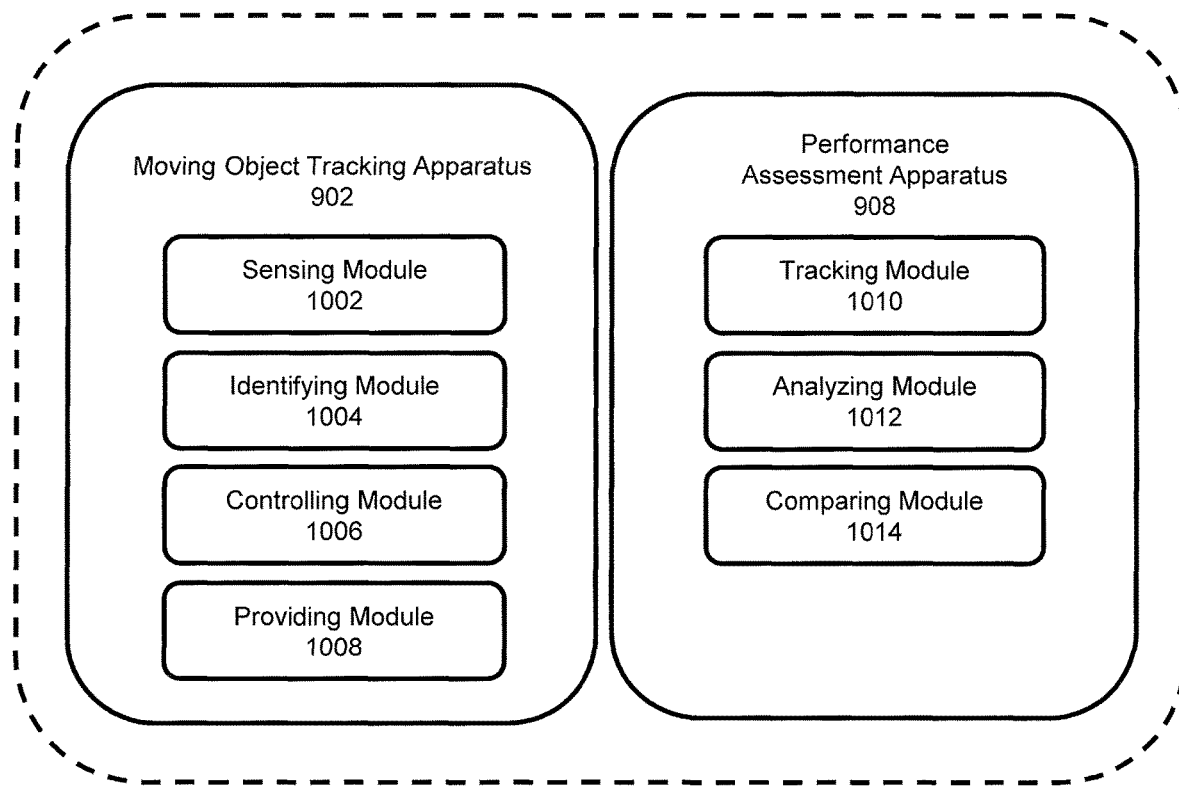
FIG. 10 shows a further schematic block-diagram of a moving object tracking apparatus and a performance assessment apparatus according to variants of the present disclosure.

In a further exemplary implementation illustrated in FIG. 10, embodiments of the method for tracking a moving object may be performed using the moving object tracking apparatus 902, which comprises a sensing module 1002, an identifying module 1004, a controlling module 1006 and a providing module 1008. The modules 1002, 1004, 1006 and 1008 may be configured as hardware entities or may be stored as computer program code in the memory 906.

Furthermore, as shown in FIG. 10, embodiments of the method for calculation the performance measure of a player of a game may be performed using the performance assessment apparatus 908, which comprises a tracking module 1010, an analyzing module 1012 and a comparing module 1014. The modules 1010, 1012 and 1014 may be configured as hardware entities or may be stored as computer program code in the memory 912.

Variants of the systems and methods as described herein use event characteristics measurements for optimized detection of HS objects with sensors and various recording devices that are controlled based on real-time analytics.

The complex analytics triggers control of recording devices may enable collaborative recording, thus several low-speed devices may achieve high time-resolution without costly equipment.

Optimized adaptive timing may follow a) the inhomogeneous events distribution during sessions, and b) the varying intrinsic characteristic times of the specific events.

The necessary optimization may be achieved, in variants, by using, for example, external sensor triggers, historical databases and machine learning.

Variants of the systems and methods as described herein may have customizable analytics logic and i/o layers. This may enable a wide range of use cases where importance of the precision of the object detection may be related to specific events, and resource optimization may be necessary.

As has become apparent from the above description of exemplary variants, the technique presented herein provides several advantages. Variants of the present disclosure may address one or more of the following objects:

- using complex triggering logic for real-time control of camera recording para meters;
- being able to recognize the change in the trajectory or other parameters related to events involving small and fast objects;
- being able to provide real-time feed of precise event parameters for sport analytics systems;
- improving time resolution, such that one is not focused on metrics based on player-related sensors where the speed is lower by several orders of magnitude;
- improving spatial resolution to determine the precise location of the ball, such that one is not focused on simple use cases, such as simple checking of border crossing by a player or a ball;
- providing a system which provides flexibility for the receiver party or for long-term learning; and
- being able to minimize a data load, as well as using adaptive control logics for the measurement devices.

Variants of the present disclosure therefore overcome the problem residing in the lack of real-time feedback of various measures of sport performance during, for example, games and/or training sessions. This situation is in contrast with other sports, for example cycling, or with the demand of various customer groups (players of various levels of professionalism, trainers and spectators).

Variants of the present disclosure further overcome the problem residing in a spectator ability to follow a game on screen being limited, as the ball may be relatively small compared to its speed.

In the present disclosure, for purposes of explanation and not limitation, specific details are outlined in order to provide a thorough understanding of the systems and methods discussed herein. It will be apparent to one skilled in the art that the systems and methods may be practiced in other variants that depart from these specific details.

Moreover, those skilled in the art will appreciate that the systems and methods explained herein may be implemented using software functioning in conjunction with a various types of processors.

It will also be appreciated that, while the variants described herein are primarily described in the context of methods and systems, the present disclosure may also be embodied in a computer program product as well as in a system comprising one or more processors and one or more memories coupled to the one or more processors, wherein the one or more memories are encoded with one or more programs that perform the features of the systems and methods disclosed herein when executed on the one or more processors.

No doubt many other effective alternatives will occur to the skilled person. It will be understood that the present disclosure is not limited to the described variants and encompasses modifications apparent to those skilled in the art and lying within the scope of the claims appended hereto.

The invention claimed is:

1. A detection system for tracking a moving object, the detection system comprising:
   a sensor for sensing an event;
   a trigger detection module coupled to the sensor, wherein the trigger detection module is configured to identify an event sensed by the sensor to be a trigger event;
   an imaging device for imaging a trajectory of an object;
   imaging device control circuitry for controlling the imaging device; and
   a trigger database;
   wherein the trigger detection module is configured to identify the trigger event by comparing, by the trigger detection module, first trigger event data obtained from the sensor to second trigger event data stored in the trigger database and obtained via the sensor at an earlier point or period in time than the first trigger event data;
   wherein the imaging device control circuitry is coupled to the trigger detection module and is configured to control the imaging device in response to the trigger event being identified by the trigger detection module; and
   wherein the imaging device is coupled to the imaging device control circuitry for providing a feedback from the imaging device to the imaging device control circuitry, and wherein the imaging device control circuitry is configured to control the imaging device in response to the feedback.

2. The detection system of claim 1, wherein the imaging device control circuitry is configured to:
   correlate the feedback with the trigger event; and
   control the imaging device based on the correlation.

3. The detection system of claim 2, wherein the correlation is based on an event type, a location, and/or a timing corresponding to the moving object being tracked.

4. The detection system of claim 2:
   further comprising correlation machine learning circuitry coupled to the imaging device control circuitry, wherein the correlation machine learning circuitry is configured to identify one or more characteristic properties and/or one or more patterns of the correlation; and
   wherein the imaging device control circuitry is further configured to control the imaging device based on the one or more characteristic properties and/or one or more patterns of the correlation identified by the correlation machine learning circuitry.

5. The detection system of claim 1:
   further comprising correlation machine learning circuitry coupled to the imaging device control circuitry, wherein the correlation machine learning circuitry is configured to identify one or more characteristic properties and/or one or more patterns of the correlation; and
   wherein the imaging device control circuitry is further configured to control the imaging device based on the identified one or more characteristic properties and/or one or more patterns of the correlation; and
   wherein the correlation machine learning circuitry and feedback machine learning circuitry are integral to a single machine learning circuitry.

6. The detection system of claim 1:
   further comprising:
   historical database for storing the trigger event data obtained via the sensor;
   a machine learning module coupled to the historical database, wherein the machine learning module is configured to identify one or more characteristic properties and/or one or more patterns of the trigger event stored in the historical database;
   wherein the machine learning module is coupled to the trigger detection module for providing information to the trigger detection module regarding the one or more characteristic properties and/or the one or more patterns identified by the machine learning module; and
   wherein the trigger detection module is further configured to identify the trigger event based on a comparison of the one or more characteristic properties and/or the one or more patterns identified by the machine learning module with a sensed trigger event.

7. The detection system of claim 6:
   wherein the trigger detection module is configured to identify the trigger event by comparing, by the trigger detection module, first trigger event data obtained from the sensor to second trigger event data stored in the trigger database and obtained via the sensor at an earlier point or period in time than the first trigger event data; and
   wherein the historical database and the trigger database are integral to a single trigger event database.

8. The detection system of claim 1:
   further comprising an imaging device database for storing one or more characteristics of the imaging device;
   wherein the imaging device database is coupled to the imaging device control circuitry; and
   wherein the imaging device control circuitry is configured to control the imaging device in response to receiving information regarding the one or more characteristics of the imaging device from the imaging device database.

9. The detection system of claim 1:
   further comprising player detection circuitry configured to identify a movement and/or position of a player and output movement data and/or position data based on the identification of the movement and/or position;
   wherein the player detection circuitry is coupled to the imaging device control circuitry; and
   wherein the imaging device control circuitry is further configured to control the imaging device in response to receiving the movement data and/or position data output by the player detection circuitry.

10. The detection system of claim 9:
    further comprising a player database coupled to the player detection circuitry; and
    wherein the player database is configured to store the movement data and/or position data output by the player detection circuitry for later retrieval.

11. The detection system of claim 10:
wherein the player database is coupled to the imaging device control circuitry; and
wherein the imaging device control circuitry is configured to control the imaging device in response to the movement data and/or position data stored in the player database and retrieved by the imaging device control circuitry from the player database.

12. The detection system of claim 1:
further comprising an image database coupled to the imaging device; and
wherein the image database is configured to store images, output by the imaging device, for later retrieval.

13. The detection system of claim 1 further comprising feedback machine learning circuitry coupled to the imaging device control circuitry, wherein the feedback machine learning circuitry is configured to identify one or more characteristic properties and/or one or more patterns of the feedback, and wherein the imaging device control circuitry is further configured to control the imaging device based on the identified one or more characteristic properties and/or one or more patterns of the feedback.

14. A system for analyzing a moving object, the system comprising:
a detection system for tracking a moving object, the detection system comprising:
a sensor for sensing an event;
a trigger detection module coupled to the sensor, wherein the trigger detection module is configured to identify an event sensed by the sensor to be a trigger event;
an imaging device for imaging a trajectory of an object;
imaging device control circuitry for controlling the imaging device;
a trigger database;
wherein the trigger detection module is configured to identify the trigger event by comparing, by the trigger detection module, first trigger event data obtained from the sensor to second trigger event data stored in the trigger database and obtained via the sensor at an earlier point or period in time than the first trigger event data;
wherein the imaging device control circuitry is coupled to the trigger detection module and is configured to control the imaging device in response to a trigger event being identified by the trigger detection module;
wherein the imaging device is coupled to the imaging device control circuitry for providing a feedback from the imaging device to the imaging device control circuitry, and wherein the imaging device control circuitry is configured to control the imaging device in response to the feedback; and
an analytics system coupled to an output layer of the detection system, wherein the analytics system is configured to analyze one or more characteristics of the object.

15. The system of claim 14, wherein the analytics system is further configured to calculate a performance measure of a player responsive to the analysis of the one or more characteristics of the object.

16. The system of claim 15, wherein the calculation of the performance measure of the player is further based on a detection of a movement and/or a position of the player.

17. The system of claim 16, wherein the calculation of the performance measure of the player is further based on the movement and/or the position of the player relative to the trajectory of the object.

18. A detection system for tracking a moving object, the detection system comprising:
a sensor for sensing an event;
a trigger detection module coupled to the sensor, wherein the trigger detection module is configured to identify an event sensed by the sensor to be a trigger event;
an imaging device for imaging a trajectory of an object;
imaging device control circuitry for controlling the imaging device;
a trigger database;
wherein the trigger detection module is configured to identify the trigger event by comparing, by the trigger detection module, first trigger event data obtained from the sensor to second trigger event data stored in the trigger database and obtained via the sensor at an earlier point or period in time than the first trigger event data; and
object analytics circuitry coupled to the imaging device and the imaging device control circuitry;
wherein the object analytics circuitry is configured to:
analyze one or more characteristics of the object; and
provide information regarding the analyzed one or more characteristics of the object to the imaging device control circuitry;
wherein the imaging device control circuitry is configured to control the imaging device in response to the analyzed one or more characteristics of the object;
wherein the imaging device control circuitry is coupled to the trigger detection module and is configured to control the imaging device in response to the trigger event being identified by the trigger detection module; and
wherein the imaging device is coupled to the imaging device control circuitry for providing a feedback from the imaging device to the imaging device control circuitry, and wherein the imaging device control circuitry is configured to control the imaging device in response to the feedback.

19. A system for analyzing a moving object, the system comprising:
a detection system for tracking a moving object, the detection system comprising:
a sensor for sensing an event;
a trigger detection module coupled to the sensor, wherein the trigger detection module is configured to identify an event sensed by the sensor to be a trigger event;
an imaging device for imaging a trajectory of an object;
imaging device control circuitry for controlling the imaging device;
an imaging device database coupled to the imaging device control circuitry and configured to store one or more characteristics of the imaging device;
a trigger database;
wherein the trigger detection module is configured to identify the trigger event by comparing, by the trigger detection module, first trigger event data obtained from the sensor to second trigger event data stored in the trigger database and obtained via the sensor at an earlier point or period in time than the first trigger event data; and
wherein the imaging device control circuitry is configured to control the imaging device in response to receiving information regarding the one or more characteristics of the imaging device from the imaging device database;

wherein the imaging device control circuitry is coupled to the trigger detection module and is configured to control the imaging device in response to a trigger event being identified by the trigger detection module;

wherein the imaging device is coupled to the imaging device control circuitry for providing a feedback from the imaging device to the imaging device control circuitry, and wherein the imaging device control circuitry is configured to control the imaging device in response to the feedback; and an analytics system coupled to an output layer of the detection system, wherein the analytics system is configured to analyze one or more characteristics of the object.

* * * * *